(12) United States Patent
Dahlqvist Leinhard et al.

(10) Patent No.: US 9,818,189 B2
(45) Date of Patent: Nov. 14, 2017

(54) METHOD OF CLASSIFICATION OF ORGANS FROM A TOMOGRAPHIC IMAGE

(75) Inventors: Olof Dahlqvist Leinhard, Linköping (SE); Magnus Borga, Linköping (SE)

(73) Assignee: ADVANCED MR ANALYTICS AB, Linkoping (SE)

( * ) Notice: Subject to any disclaimer, the term of this patent is extended or adjusted under 35 U.S.C. 154(b) by 347 days.

(21) Appl. No.: 14/379,221

(22) PCT Filed: Feb. 17, 2012

(86) PCT No.: PCT/SE2012/050178
§ 371 (c)(1),
(2), (4) Date: Jan. 20, 2015

(87) PCT Pub. No.: WO2013/122523
PCT Pub. Date: Aug. 22, 2013

(65) Prior Publication Data
US 2015/0125056 A1    May 7, 2015

(51) Int. Cl.
*G06T 7/00* (2017.01)
*A61B 5/055* (2006.01)
(Continued)

(52) U.S. Cl.
CPC ............ *G06T 7/0014* (2013.01); *A61B 5/055* (2013.01); *A61B 6/032* (2013.01); *A61B 6/037* (2013.01);
(Continued)

(58) Field of Classification Search
None
See application file for complete search history.

(56) References Cited

U.S. PATENT DOCUMENTS 6,587,702 B1 * 7/2003 Ruchti ................. A61B 5/0059
600/306
2008/0188741 A1    8/2008 Mallya et al.
(Continued)

FOREIGN PATENT DOCUMENTS

WO    2011039515 A1    4/2011
WO    2012012768 A1    1/2012

OTHER PUBLICATIONS

Dahlqvist Leinhard et al., "Quantitative abdominal fat estimation using MRI," 19th International Conference on Pattern Recognition, ICPR 2008.*

(Continued)

*Primary Examiner* — Matthew Bella
*Assistant Examiner* — Soo Shin
(74) *Attorney, Agent, or Firm* — Michael G. Johnston; Moore & Van Allen, PLLC (57) ABSTRACT

The present invention relates to a method for classification of an organ in a tomographic image. The method comprises the steps of receiving (102) a 3-dimensional anatomical tomographic target image comprising a water image data set and a fat image data set, each with a plurality of volume elements, providing (104) a prototype image comprising a 3-dimensional image data set with a plurality of volume elements, wherein a sub-set of the volume elements are given an organ label, transforming (106) the prototype image by applying a deformation field onto the volume elements of the prototype image such that each labeled volume element for a current organ is determined to be equivalent to a location for a volume element in a corresponding organ in the target image, and transferring (108) the labels of the labeled volume elements of the prototype image to corresponding volume elements of the target image.

13 Claims, 5 Drawing Sheets

(51) Int. Cl.
  *A61B 6/03* (2006.01)
  *A61B 6/00* (2006.01)
  *G06T 7/33* (2017.01)
  *G06T 7/11* (2017.01)
  *G06T 7/174* (2017.01)

(52) U.S. Cl.
  CPC .............. *A61B 6/5247* (2013.01); *G06T 7/11* (2017.01); *G06T 7/174* (2017.01); *G06T 7/337* (2017.01); *A61B 6/5217* (2013.01); *G06T 2207/10081* (2013.01); *G06T 2207/10088* (2013.01); *G06T 2207/10104* (2013.01); *G06T 2207/30056* (2013.01)

(56) References Cited

U.S. PATENT DOCUMENTS

| | | |
|---|---|---|
| 2008/0240527 A1 | 10/2008 | Keller |
| 2008/0285822 A1 | 11/2008 | Kaus et al. |
| 2009/0028403 A1 | 1/2009 | Bar-Aviv et al. |
| 2009/0185731 A1 | 7/2009 | Ray et al. |
| 2009/0226057 A1* | 9/2009 | Mashiach ............... G06T 5/008 382/128 |
| 2010/0002921 A1 | 1/2010 | Fenchel et al. |
| 2010/0054525 A1 | 3/2010 | Gong et al. |
| 2010/0054563 A1 | 3/2010 | Mendonca et al. |
| 2010/0098309 A1 | 4/2010 | Graessner et al. |
| 2010/0260394 A1 | 10/2010 | Meetz et al. |
| 2010/0295848 A1* | 11/2010 | Grewer ............... G06T 7/0081 345/419 |
| 2011/0007959 A1 | 1/2011 | Schulz et al. |
| 2011/0019889 A1* | 1/2011 | Gering ................. A61B 6/032 382/131 |
| 2011/0081055 A1 | 4/2011 | Bell et al. |
| 2011/0160546 A1 | 6/2011 | Madsen |
| 2011/0317900 A1* | 12/2011 | Pal ....................... G01R 33/481 382/131 |
| 2012/0281900 A1* | 11/2012 | Rueckert ............... G06K 9/468 382/131 |

OTHER PUBLICATIONS

Jahanshad et al., "Genetic influences on brain asymmetry: A DTI study of 374 twins and siblings," NeuroImage, vol. 52 (2010), pp. 455-469.*

Rydell et al., "Phase Sensitive Reconstruction for Water/Fat Separation in MR Imaging Using Inverse Gradient," MICCAI 2007, Part I, LNCS, 4791, pp. 210-218.*

Romu et al., "Fat Water Classification of Symmetrically Sampled Two-Point Dixon Images Using Biased Partial Volume Effects," Proc. Intl. Soc. Mag. Reson. Med. 19 (2011), pp. 2711.*

Friman et al., "A General Method for Correction of Intensity Inhomogeniety in Two Point Dixon Imaging," Proc. Intl. Soc. Mag. Reson. Med. 17 (2009), pp. 4637.*

Leinhard et al., "Water fat shift displacement artifact correction in two point Dixon imaging," Proc. Intl. Soc. Mag. Reson. Med. 16 (2008), pp. 1384.*

Leinhard et al., "Intensity inhomogeneity correction in two point Dixon imaging," Proc. Intl. Soc. Mag. Reson. Med. 16 (2008), pp. 1519.*

International Search Report dated Nov. 22, 2012.

Leinhard, O. Dahlqvist, et al.; "Quantitative abdominal fat estimation using MRI," Pattern Recognition, 2008, ICPR 2008, 19th International Conference on Dec. 8-11, 2008, IEEE, pp. 1-4.

Knutsson, H., et al., Normalized and differential convolution: Methods for interpolation and filtering of incomplete and uncertain data, Proceedings of Computer Vision and Pattern Recognition (CVPR'93), 1993, pp. 515-523.

* cited by examiner

METHOD OF CLASSIFICATION OF ORGANS FROM A TOMOGRAPHIC IMAGE

TECHNICAL FIELD

The present disclosure relates to classification of organs in an image, and especially to the classification of organs in a 3-dimensional anatomical tomographic image comprising a water image data set and a fat image data set.

BACKGROUND

In 3-dimensional tomographic medical imaging, identification of different body tissues and organs, such as muscles, is an important part of the medical interpretation of the images. The size, shape and composition, and their variations over time, of different organs can be an important piece of information in many clinical questions. The identification of such features is in general a manual process, which includes manually identifying a specific organ and possibly labeling it in the image. The present image may, after a complete identification and analysis process, comprise a plurality of labels for different organs. Points, or voxels, in the 3-dimensional image may thereby represent a location of an organ.

However, when a new image is taken of a different body, the identification process needs to be done all over again. The identification and analysis of a previous image is not possible to reuse on a new image.

Consequently, there is a need for a method of identifying organs in a 3-dimensional tomographic image, which may be performed automatically.

SUMMARY OF THE INVENTION

It is an object of the present invention to provide an improved solution that alleviates the mentioned drawbacks with present devices. Furthermore, it is an object to provide a method of classification of organs from a tomographic image.

This is achieved according to an aspect of the invention wherein a method for classification of an organ in a tomographic image is provided. The method comprises the steps of receiving a 3-dimensional anatomical tomographic target image comprising a water image data set and a fat image data set, each with a plurality of volume elements, providing a prototype image comprising a 3-dimensional image data set with a plurality of volume elements, wherein a sub-set of the volume elements are given an organ label, transforming the prototype image by applying a deformation field onto the volume elements of the prototype image such that each labeled volume element for a current organ is determined to be equivalent to a location for a volume element in a corresponding organ in the target image, and transferring the labels of the labeled volume elements of the prototype image to corresponding volume elements of the target image.

In the prototype image, the sub-set of volume elements may comprise at least one labeled volume element. The at least one labeled volume element may have a label naming the current organ in which the labeled volume element is located in the prototype image. Such label may be "biceps", "liver" or any name of an organ. When transforming the prototype image, the volume elements in the prototype defining the edge of the current organ may be moved to a location corresponding to a location for a corresponding edge in the target image. An organ volume in the prototype image defined by said edges may then change in shape and position to conform to the shape and position of the corresponding organ in the target image. The at least one labeled volume element inside the organ volume in the prototype image may then also be moved as a consequence to the edge movement, but may be kept inside the organ volume. The labeled volume element in the organ volume in the transformed prototype image may then have a corresponding volume element in the target image that with very high probability also is located inside a corresponding organ. The label of the labeled volume element in the prototype image may in the next step be transferred to the corresponding volume element location in the target image.

The result from this process may be an identification of locations of one or more organs in a target image. This organ is thereby classified by the label. Further, the amount of transformation of the prototype image to conform to the shape of the target image may be analyzed. For instance, the prototype image may be an image of the same body as the target image, but at an earlier point of time. The change of properties of a specific organ over the time between the two images may then be analyzed and visualized.

The volume elements may be voxels in the 3-dimensional images. All steps in the method may be performed automatically, for instance by a computer device. By organ it is meant any muscle or fat tissue or other inner organs in a body.

The method according to the present invention may enable a mapping of Hounsfield attenuation values defined in the prototype image to an MR (Magnetic Resonance) image. MR images may then be used for attenuation correction in PET (Positron Emission Tomography) imaging.

Extra robustness in the classification may be achieved by using the multi-field data in the water and fat image data sets. For example, the labeled volume elements for an organ in the target image may be labeled as adipose tissue. If the labeled volume elements may be multiplied with the fat image data set, and labeled volume element wrongly transferred into a water area in the target image may automatically be removed.

In one embodiment, similarly labeled volume elements in the target image may define an organ volume representing a current organ, and wherein the method may further comprise a step of extending said organ volume to the entire organ based on properties in the target image.

By extending the organ volume in the target image, the organ may be completely segmented and visualized. The organ volume may be a visualization of a substantially entire organ in the target image. The image data in the target image may be analyzed to define the extended organ volume. Volume elements in the target image may be analyzed, for instance based on their intensity level, to determine an extension of the organ volume. The target image comprising segmented and classified organs may be used for determination of the volume of each segmented organ. Further, due to the multi-field data in the target image, comprising both water and fat image data, the segmented and classified target image may be used for measuring the fat and water content in a specific organ, for instance measuring the percentage of fat in the liver or the fat content in a muscle, possibly compared to the water content in the same muscle.

In a further embodiment, the step of extending the organ volume may comprise detecting an edge of the organ in the target image.

Inside the organ in the target image the intensity level of the volume elements may be substantially homogeneous. At the edges of the organ, a change in the intensity level in the volume elements may be detected. By detecting the edge of the organ in the target image, the boundaries of the organ volume may be detected, which may define the organ volume. Based on the labeled volume elements inside the organ volume, the entire organ volume, now defined by the detected boundaries, may be provided with the same label. The organ in the target image may thereby be classified and segmented by being given a label.

In a yet further embodiment, the method may further comprise a step of manually entering a label to, or removing a label from, a volume element in the target image, wherein said manual step may be followed by a redefinition of the organ volume referring to the present label.

In some occasions, when transferring the labeled volume element from the prototype image to the target image, the labeled volume element in the target image may end up close to the boundary of the organ volume. This may cause a wrongly defined organ volume due to a labeling of a volume element which should not be labeled or be part of the organ volume. The method may then comprise a step of manually removing a labeled volume element in the target image. This step may be followed by a redefinition of the organ volume. This may be done by, starting with the remaining labeled volume elements for the current organ, redetermining the extension of the organ volume based on the image properties in the target image. A redetermination of the extension of the organ volume may also be performed when a label is added to a volume element. A label may be added to increase the correctness in the volume extension determination.

In one embodiment, the step of transforming the prototype image may comprise applying a non-rigid co-registration of the prototype image onto the target image to increase the similarity between the prototype image and the target image, and wherein the non-rigid co-registration may provide said deformation field representing a deformed prototype image.

The purpose of the non-rigid co-registration may be to maximize the similarity between the prototype image and the target image. There are several known non-rigid co-registration methods, such as Demons (J.-P. Thirion. Image matching as a diffusion process: an analogy with Maxwell's demons. Medical Image Analysis, 2(3), 1998) and Morphon (Knutsson H, Andersson M. Morphons: Segmentation using elastic canvas and paint on priors. In: IEEE International Conference on Image Processing ICIP 2005, 2005). Any of these may be used to determine a deformation field which defines how the prototype image may be deformed or transformed in order to best fit the target image. Such method may provide a reliable determination of the deformation field, which may increase the probability that a labeled volume element in the prototype image may end up in a corresponding organ in the target image.

In one embodiment, said tomographic image may be received from a magnetic resonance (MR) scanner or a computed tomography (CT) scanner.

A magnetic resonance scanner or a computed tomography scanner may provide a 3-dimensional target image comprising a water image data set and a fat image data set.

In another embodiment, the method may further comprise the step of removing the label of a first labeled volume element in the target image based on an analysis of said first labeled volume element compared to a similarly labeled second volume element in the target image.

It may occur that two similarly labeled volume elements are not located in a common organ, i.e. one of the labels may be wrongly set. To identify such wrongly set label, two commonly labeled volume elements may be compared to identify any differences, which differences may indicate a misplaced label. Such analysis and comparison may for instance be based on intensity level in the labeled volume elements.

In a further embodiment, said analysis may comprise an analysis of said first labeled volume element in the water data set and in the fat image data set compared to the similarly labeled second volume element in the water image data set and the fat image data set.

Since the target image comprises both a water image data set and a fat image data set, each volume element in the target image may have both a water value from the water image data set and a fat value from the fat image data set. By comparing the water and fat values for a labeled volume element in the target image with the corresponding labeled volume element in the prototype image, a wrongly transferred labeled volume element may be identified. Such wrongly transferred labeled volume element may then be removed to improve the defined organ volume. The comparison may be based on intensity level for the volume elements in the respective water and fat image data sets.

In a further embodiment, the step of removing a first labeled volume element may comprise determining a water-fat relationship for the first labeled volume element, comparing said water-fat relationship with a corresponding water-fat relationship for the similarly labeled second volume element in the target image, and removing the first labeled volume element based on said comparison.

The water value and the fat value for a volume element in the target image may be compared to analyze the properties for that volume element. This may provide a water-fat relationship for that volume element based on intensity levels for the volume element in the image data sets. This information may be used for determining the water and fat content in that point in the body represented by the target image. Different organs may have different water-fat relationship due to different substance composition in the organs. The determination of whether a label of a labeled volume element is wrong may be based on that two similarly labeled volume elements should have a substantially similar water-fat relationship, or at least have water-fat relationships within a common range. For instance, a muscle may have different water-fat relationship compared to another organ such as a liver. Further, close to a muscle, and also interspersed into the muscle, there may be fat which is not a part of the muscle. When defining the organ volume for that muscle, the interspersed fat may be wanted to be disregarded. The water-fat relationship in a volume element in the fat may be different from the water-fat relationship in the muscle. The fat may then be identified and the label for the volume element in the fat may be removed. In one embodiment, a fat volume may be defined in the same way as the organ volume. The fat volume may then be disregarded from the organ volume of the muscle.

In another embodiment, said analysis may be based on the first and second labeled volume elements' geometric location in the target image.

A labeled volume element that is located close to an outer edge of the body in the target image, which edge may represent the skin of the body in the target image, may be determined to be uncertain because it may be a large risk that that label is misplaced. By determining the geometric location of two or more similarly labeled volume elements, a labeled volume element close to the outer edge may be disregarded, i.e. the label may be removed from that volume element. This may increase the correctness of the extension determination of the organ volume for the organ represented by said label.

In another embodiment, the prototype image may comprise an indicator on which said analysis is based.

The prototype image may comprise an indicator or criterion for a specific organ which may be used in the analysis of the labeled volume elements. Such indicator or criterion may be comprised in the label that is transferred from the prototype image to the target image. A certain organ label may thereby comprise an indicator or criterion for that organ, on which indicator or criterion the analysis between two similarly labeled volume elements referring to that organ is based when determining the correctness of the locations of said labeled volume elements. The analysis may be based on intensity level for a volume element in the target image, the water image data set and/or the fat image data set.

In one embodiment, the step of providing a prototype image may comprise providing a plurality of prototype images, wherein the step of transforming the prototype image may comprise transforming the plurality of prototype images, which step may be followed by a step of determining which of the transformed prototype images that best corresponds to the target image.

By using a plurality of prototype images, a better match between the prototype image(s) and the target image may be achieved. When each of the prototype images have been transformed, a comparison between each of the prototype images and the target image may be performed for the decision of which of the prototype images that best matches the target image. This provides a further increased similarity between the selected prototype image and the target image. The comparison may be based on a final value of a utility function being optimized in the non-rigid co-registration process, or on a similarity measure, such as correlation or the mutual information, between the deformed prototype image and the target image. The prototype image that provides a value or measure corresponding to a best match between the prototype image and the target image may be selected to be used as final prototype image.

In another embodiment, said prototype image may be a mirrored copy of said target.

Many organs, such as muscles, are similar in size and position between a left and a right half of a human body. The method according to claim 1 may thereby be used for comparing organs in the left half with corresponding organs in the right half. A mirrored copy of the target image may be made to be used as prototype image. The right side of the prototype image may thereby be compared with the left side of the target image, and the left side of the prototype image may be compared with the right side of the target image. By transforming the prototype image to conform to the target image, a difference between corresponding organs in the image, i.e. two sides of the body in the target image, may be detected based on the amount of transformation needed on the prototype image to conform to the target image. For instance, the left thigh muscle in a body may be compared with the right thigh muscle to detect differences in size. Such difference may be important to detect to prevent a future wearing injury. A deformation field may thereby be provided representing the difference between the two sides in the body. Such deformation field may be visualized for the entire images such that differences may be analyzed. A further prototype image may be used for classifying the organs in the target image and/or the mirrored image. The additional prototype image may comprise labeled volume elements as described above, and may be transformed such that the labeled volume elements may be transferred to the target image. The method may thereby provide an automatic process for detecting a difference between the two sides of a body image for a specific, classified, organ. It may further quantify the deformation field for different organs in the target image.

In one embodiment, the method may further comprise a step of calibrating the target water image data set based on labeled organs in the water image data set, wherein each labeled volume element in the target water image data set labeled as a particular organ is given a predetermined water value for that particular organ.

Several organs in a body may comprise a large amount of water, but the water content and the water signal strength may vary between different organs. The signal strength in the water image may also vary over the image due to physical limitations in the imaging device. To achieve a normalized, quantitative image of a body from the target water image data set, each organ may first be identified as presented above. To normalize the water image, each labeled organ volume element may be given a predetermined value in the water image data set. The predetermined water value may be specific for a particular organ. Information regarding the predetermined water value for a particular organ may be comprised in a label in the prototype image. The same water value in the target image may represent the same physical properties in the target image. The predetermined water value for a labeled volume element in a particular organ may be set not only based on the actual water value in that volume element, but also based on tissue structure in that entire particular organ. The predetermined water value may not only represent the amount of water in that volume element, but also structure properties of the tissue in that organ. The predetermined water value for the labeled volume element may be compared with the actual water value for that volume element to establish a difference between the two values.

In a further embodiment, the method may further comprise a step of interpolating values of the labeled volume element into a continuous organ volume based on the predetermined water value in the labeled volume element.

By interpolating the values of the normalized labeled volume element, a homogeneous organ volume may be achieved. This homogenous volume may then be used for calibrating the corresponding part of the water image volume in order to obtain a quantitative water image. The interpolation of the values of the labeled volume elements, based on the predetermined water value, may be performed in a corresponding manner as the interpolation method for fat values described in EP2283376. All volume elements in a particular organ may thereby have a common water value to provide a normalized, homogeneous, water image. For instance, a labeled muscle volume element may in the water image data set have an intensity value of 0.8. Since it is identified as present in a muscle organ, its water value, i.e. intensity value in the water image, may be set to 1. The scale of the predetermined water value may be selected based on the information wanted from that particular organ. If muscles are identified and calibrated, a predetermined water value of 1 may represent 100 percent muscle tissue in that volume. If a liver is identified and calibrated, the predetermined water value 1 may represent something else. The interpolation may be based on the difference between the predetermined water value and the actual water value of the labeled volume element.

This organ normalization method may enable a volume rendering of an MR target image using transfer functions. It may further enable an improvement of the Hounsfield attenuation value mapping by providing an improved estimation of the Hounsfield attenuation value in the organs.

In a yet further embodiment, said predetermined water value may be subtracted with that labeled volume element's fat value in the fat image data set.

Each labeled volume element identified as present in a particular organ, for instance a muscle, may be given a predetermined water value. The predetermined water value may be subtracted with a fat value for the same volume element from the fat image data set. The water value and fat value from the image data sets may be represented by intensity values for the volume element in the two image data sets. For instance, a labeled volume element may in the water image data set have an intensity value of 0.8. Since it is identified as present in a muscle organ, its water value, i.e. intensity value in the water image, is set to 1. In the fat image data set, the same volume element may have an intensity value of 0.1. The set water value 1 may then be subtracted with the fat value 0.1, equals 0.9. This may be performed in order to provide a normalized muscle structure, but with kept water and fat content information in the muscle organs.

The identification of image volume elements belonging to a specific organ may be based on a variety of criteria and combinations thereof.

A criterion to identifying volume elements with high probability of containing a specific organ or tissue type may be based on a thresholding operation where volume elements with intensity levels lower than a lower limit or higher than an upper limit are excluded. Skin may be removed or identified by an operation on image volume element outside an eroded body mask, where the body mask may be created using a thresholding operation on a combined fat and water image followed by an operation closing holes in the created body mask.

Image volume elements with a high probability of being affected by partial volume effects may be excluded by an operation where volume elements belonging to a dilated fat mask image are excluded. The fat mask image may be created by identifying all volume elements with fat signal intensity level over a certain threshold level and with a high value of the fat image divided by the fat plus water image.

Regions with high probability to be falsely classified as belonging to a certain organ may be excluded by indicating a corresponding label field in the label image corresponding to the prototype image according to claim 1.

The present invention may be used in a variety of applications, such as: Muscle atrophy characterization, monitoring of temporal changes in muscle volume during interventions, injury rehabilitation; Muscle tissue asymmetry measurements; Volume rendering of using transfer functions also for MR images; Mapping of Hounsfield attenuation values defined in a prototype to an MR image in order to use MR images for attenuation correction in PET imaging; and Body composition measurement, using the described technique the following body composition characteristics may be measured:

VAT—Visceral adipose tissue volume;
SAT—Subcutaneous adipose tissue volume;
TAT—Total adipose tissue volume;
Liver volume;
Liver fat volume;
Muscle volume;
Muscle fat volume;
Brain volume;
Bone marrow volume;
Body volume (excluding or including low signal intensity regions related to the airways and the lungs);
Volume of other organs with high content of water. These organs may be determined by identifying water image volume elements with intensity level above a certain threshold level in image regions without other organ definitions. The water content in the identified water image data set elements may also be corrected by subtracting the integrated fat volume in the corresponding volume elements in the fat image data set;

Brown adipose tissue related image volume. This may be identified by integrating image volume elements with an intensity within a specific interval of fat/(fat+water) ratio also fulfilling a criteria of having sufficient object size to allow separation of volume elements fulfilling the fat and water ratio criteria due to partial volume effects. This criterion may furthermore be sharpened by anatomical definitions in the prototype image used for image classification to exclude regions in the image with high probability of false identification of brown adipose tissue.

Furthermore, if the body composition measurement is combined with accurate weighing of the imaged subject tabulated densities of different organs may be utilized to characterize the mass of organs without signal visible in conventional MRI experiments, such as bone and solids.

BRIEF DESCRIPTION OF THE DRAWINGS

The invention will in the following be described in more detail with reference to the enclosed drawings, wherein.

DESCRIPTION OF EMBODIMENTS

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements.

Figure 1:
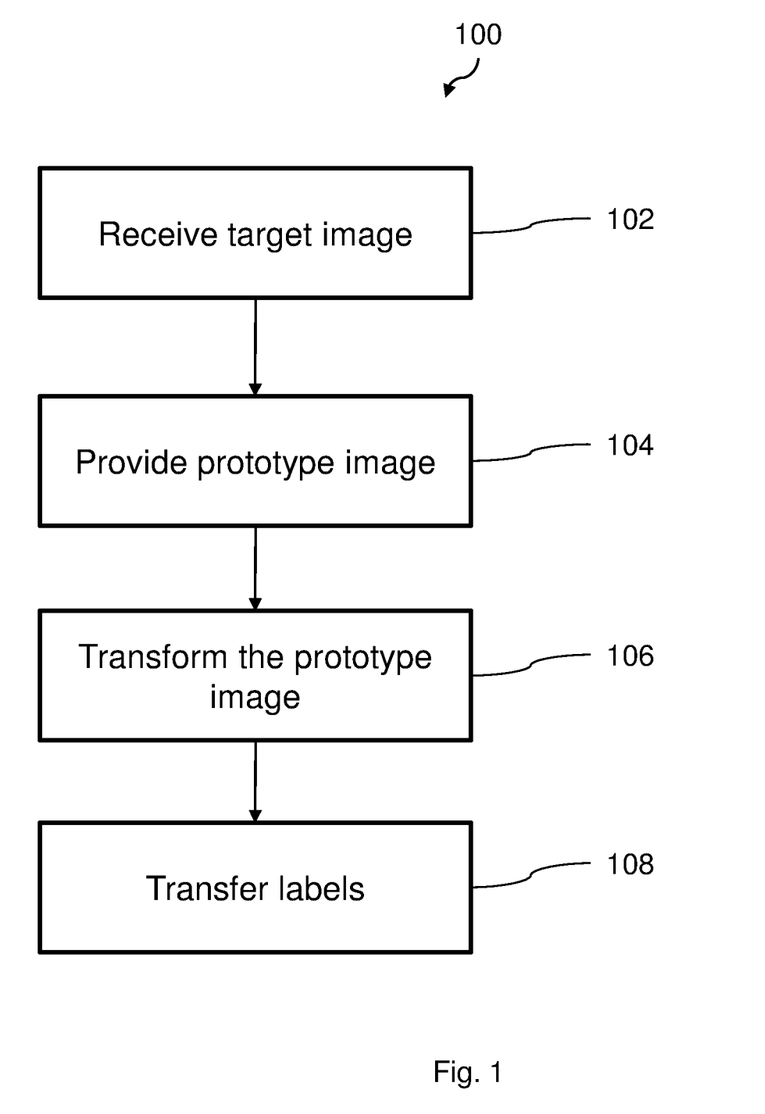
FIG. 1 shows a flow chart of a method according to an embodiment of the invention.

FIG. 1 illustrates a flow chart of a method 100 according to an embodiment, for registration and classification of organs in a body. The method 100 comprises a first step 102 wherein a 3-dimensional tomographic image is received. The image is provided from a medical scanning apparatus, such as a magnetic resonance (MR) scanner or a computed tomography (CT) scanner. The received tomographic image is a target image, i.e. the image in which organs is to be registered and classified. The target image may be a 3-dimensional tomographic image of a human body or a part of a human body.

The target image is a multi-field data image, comprising a water image data set and a fat image data set. Each volume element (voxel) in the target image has one data value in the water image data set and one data value in the fat image data set.

In step 104, a prototype image is provided. The prototype image is also a 3-dimensional tomographic image, preferably also with an origin from a MR or CT scanner. In a (not shown) pre-step, the prototype image is created, wherein an operator manually identifies different organs in the body in the prototype image. In an identified organ, the operator sets a label to at least one volume element in the prototype image, within the identified organ. The identified organ is thereby classified in the prototype image. The prototype image may comprise a plurality of different labels for different organs. The creation of the prototype image is a onetime operation. The same prototype image is used for many classification processes, for many target images.

In step 106, a deformation field is calculated and used for transforming the prototype image. The deformation field is calculated on how a data set in the prototype image for a specific organ should be deformed in order to best conform with the shape of the corresponding organ in the target image. Such calculation is performed on the entire prototype image and the prototype image is transformed, or deformed, correspondingly.

Inside a volume of an organ in the prototype image, at least one volume element is provided with a label as presented above. By applying the deformation field on the prototype image, such that the shape of the current organ in the prototype image conforms to the corresponding organ in the target image, the probability of said labeled volume element in the prototype image ending up inside the corresponding organ in the target image is high. The labeled volume element is then transferred, according to step 108, to the target image. Due to the deformation of the prototype image, wherein the shape of an organ volume in the prototype image is deformed to conform with a corresponding organ volume in the target image, and which organ volume in the prototype image encloses a labeled volume element for the current organ, that labeled volume element in the prototype image can be transferred to the target image, and thereby, with high accuracy, label that organ in the target image.

All these steps can be performed automatically, for instance by a computer device, with the target image and the prototype image as input, and without a need of manual interaction.

The result from a classification, i.e. the target image with identified and labeled organ volumes, can after analysis be used as a new prototype image in a future classification process.

Figure 2:
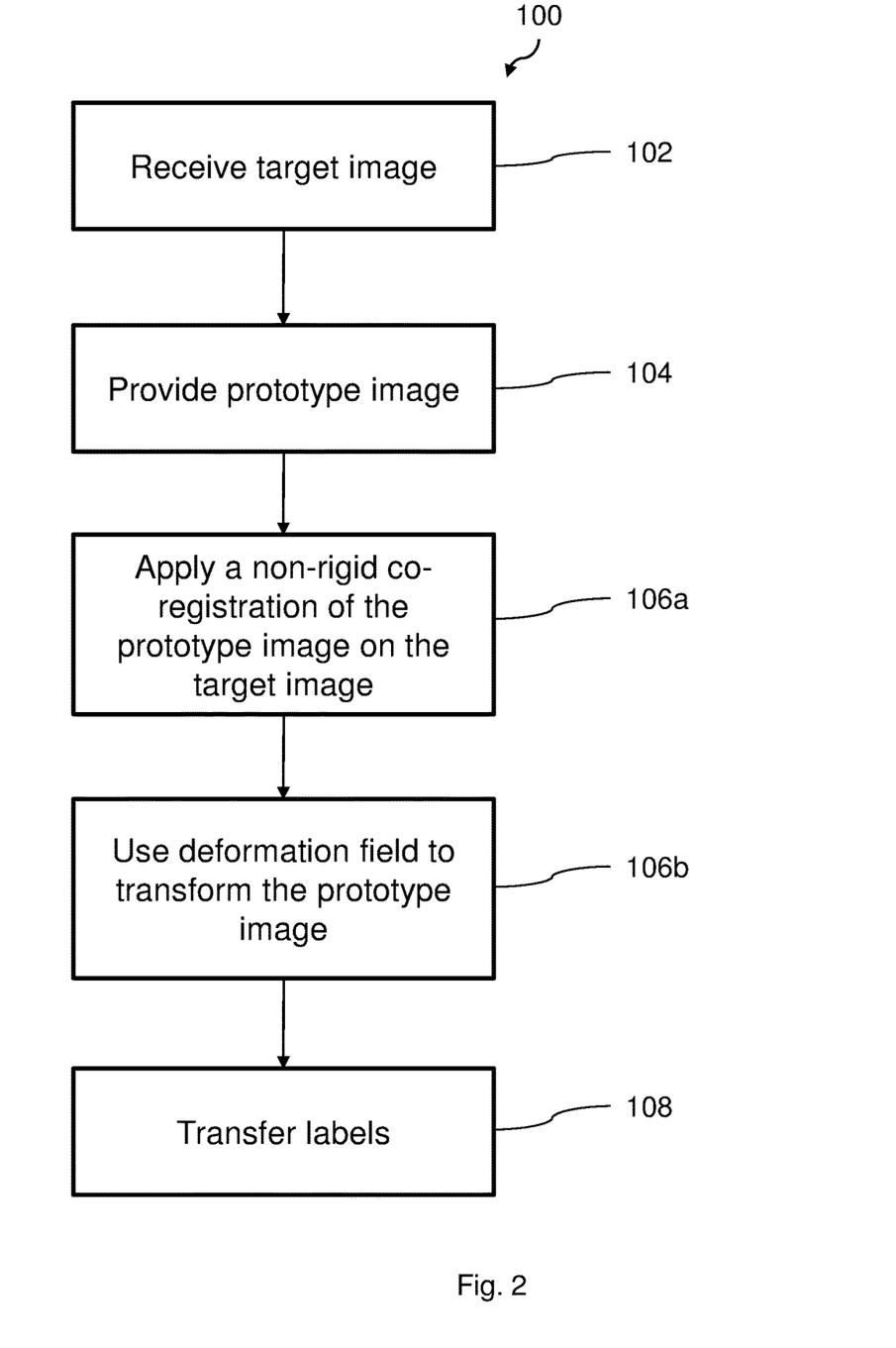
FIG. 2 shows a flow chart of a method according to an embodiment of the invention.

FIG. 2 illustrates the method 100 in an embodiment wherein the step 106 comprises two steps 106a, 106b. The first sub-step 106a comprises applying a non-rigid co-registration of the prototype image on the target image. The skilled person may know a plurality of non-rigid co-registration methods to apply on two images. As example, such non-rigid co-registration may be Demons or Morphon (see reference above).

The non-rigid co-registration may in general be described as follows. Edges of an organ, or another contrasty part, in the prototype image are defined by analyzing the image. The edges are defined based on properties of volume elements in the image, for instance based on intensity level in the volume elements. A gradient may thereby be detected to define an edge. The prototype image is compared to the target image and corresponding edges or contrasty parts in the target image, adjacent to the corresponding edge location in the prototype image, are identified. The difference in location of corresponding edge volume elements in the two images are calculated to identify how the edge volume elements in the prototype image should be moved to reach a corresponding location as in the target image. By applying this to an entire edge of an organ volume in the prototype image, a deformation field defining how the edge volume elements defining the shape of the organ volume should be moved to conform to the shape of the corresponding organ volume in the target image is provided. Such non-rigid co-registration provides a deformation field for the prototype image.

In the next sub-step 106b, the deformation field is used on the prototype image to deform the prototype image to maximize the similarity between the two images. This is performed on the base of the entire body visualized in the images.

If the non-rigid co-registration had been perfect, the transformation of these labels according to the deformation field would perfectly label all the corresponding volume elements in the target image. However, due to anatomical variations in many organs and tissues in a body and the fact that the non-rigid co-registration process must be constrained to relatively smooth deformations, a perfect fit of all prototype volume elements to the corresponding target volume elements is, in many cases, not possible. This is why only a sub-set of the volume elements is labeled. These labeled volume elements are chosen such that they, with high probability, maintain a correct label after the transformation.

Figure 3:
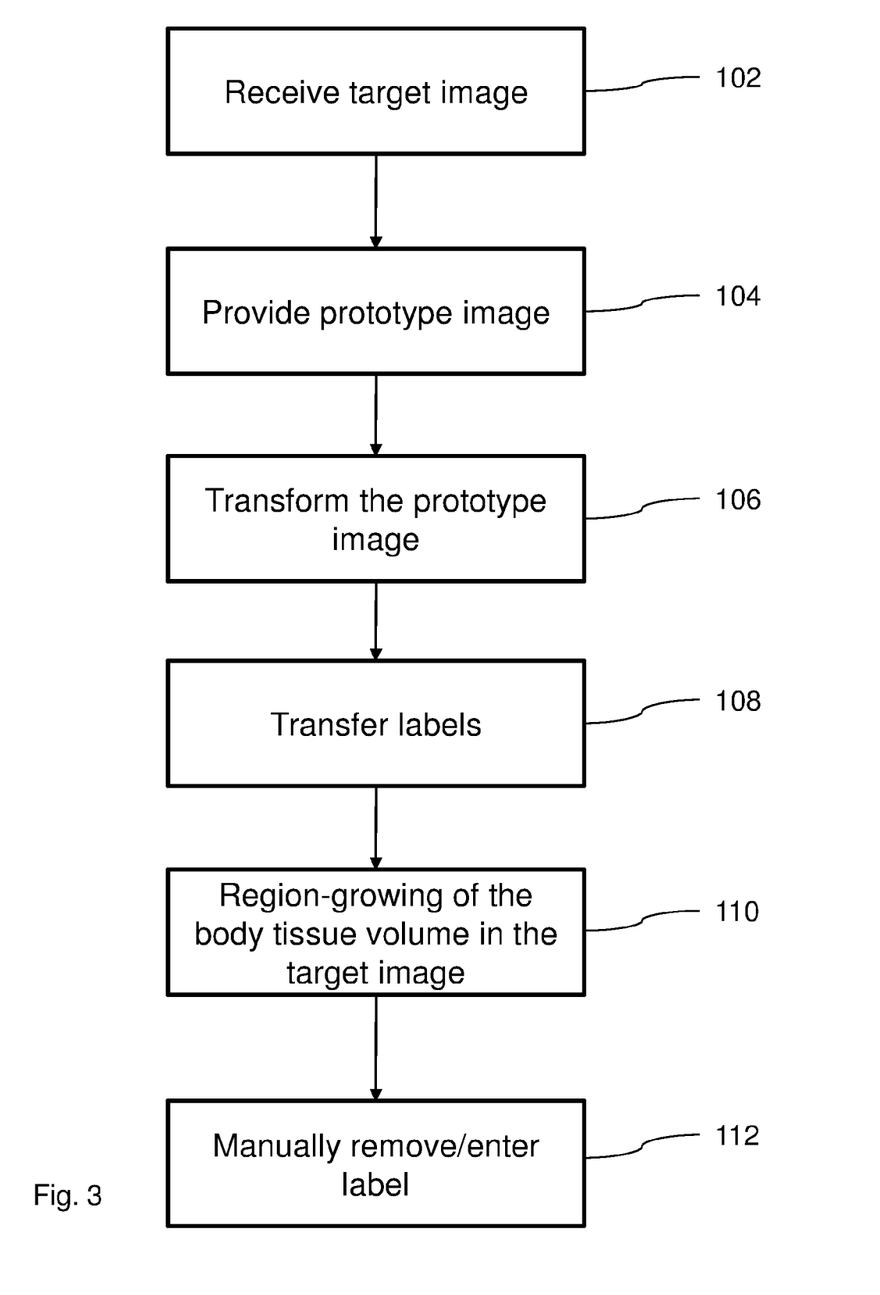
FIG. 3 shows a flow chart of a method according to an embodiment of the invention.

FIG. 3 illustrates the method 100 further comprising two respectively optional steps. In step 108, the labeled volume elements for an organ in the prototype image is transferred to the target image. A target image is thereby achieved comprising a labeled volume element for an organ, thereby classifying that organ in the target image. In order to label the remaining volume elements in the target image, a "region-growing" segmentation step 110 is applied, using the transferred labeled volume elements as initiation. This kind of segmentation methods starts at one or more defined starting points, i.e. the labeled volume elements. From there the set of labeled volume elements grows until a stopping criterion is met. Such a stopping criterion can be e.g. a visible interface (gradient) in the target image, or that the labeled region (organ) meets another region with a contradicting label (e.g. another organ or image background). There are numerous different region-growing based methods, e.g. Watershed or IFT (Image Foresting Transform". Falcao, A. X. Stolfi, J. de Alencar Lotufo, R.: "The image foresting transform: theory, algorithms, and applications", In PAMI, 2004).

A plurality of organs in the target image can be segmented and classified. The 3-dimensional target image may then visualize the labeled organs. When the organs have been segmented and classified, they may further each be given an individual color in the target image, which would further enhance the visualization of the organs in the target image.

When visualizing the final classification result, erroneous labels may be identified. In such cases, it is possible to correct this miss-classification by manually adding new labeled volume elements with correct labels in the wrongly classified regions using e.g. IFT. It is also possible to manually remove labels on volume elements that eventually have transformed into the wrong organ. After adding one or a set of new labels, the region-growing is re-calculated and the new result is visualized. This process is repeated until a satisfactory result is obtained.

Figure 4:
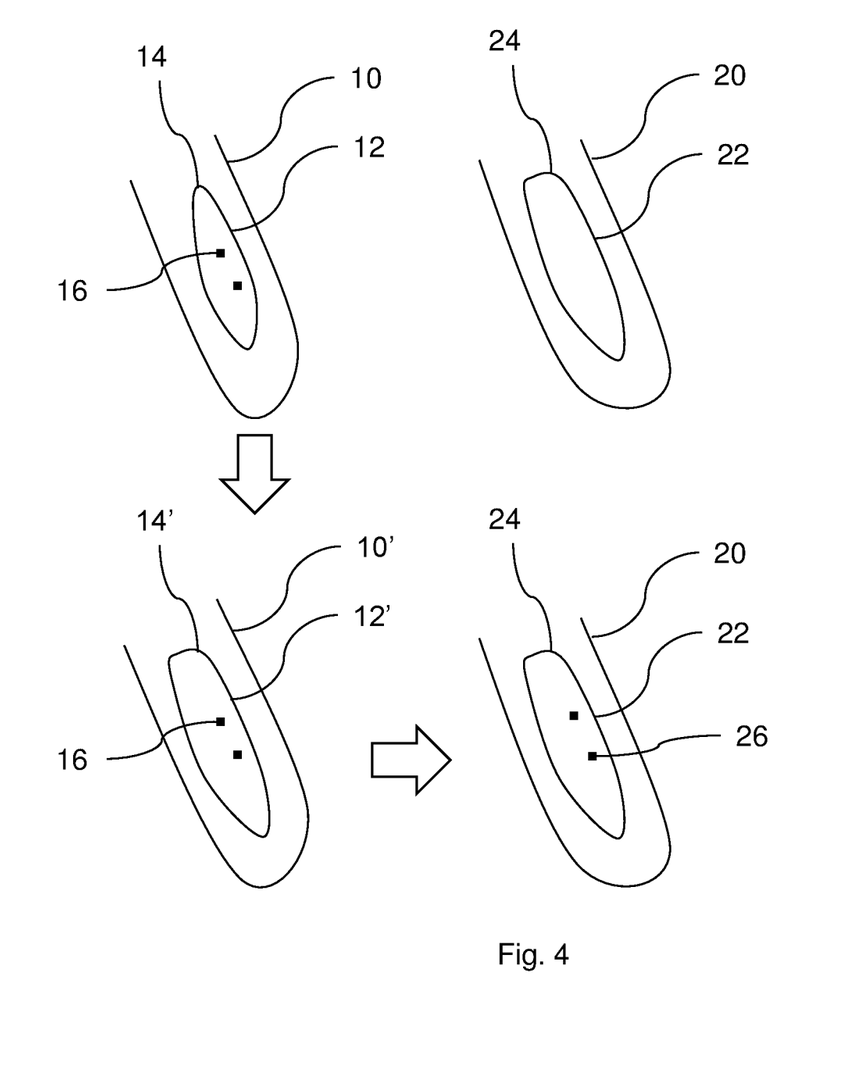
FIG. 4 shows a schematic view of body images used in a method according to an embodiment of the invention.

FIG. 4 illustrates the method 100 in view of a schematic partial image representation. In the figure, a prototype image 10 and a target image 20 is provided. The images 10, 20 are illustrated as a part of a body image. The prototype image 10 comprises an organ 12 which encloses two manually entered labeled volume elements 16. The target image 20 comprises a corresponding organ 22. In the step 106 of transforming the prototype image 10, the edge 14 of the organ 12 is detected in the prototype image 10. The corresponding edge 24 for the organ 22 in the target image is detected. A deformation field determines how the edge 14 of the prototype image 10 should be deformed to conform to the shape of the edge 24 in the target image 20. The deformation field is applied on the prototype image 10 which results in a deformed prototype image 10' comprising a deformed organ 12' with a deformed edge 14'. The labeled volume elements 16 are still enclosed in the organ 12'. The location of the labeled volume elements 16 in the organ 12' may have changed slightly due to the deformation of the organ 12'. However, they will still be enclosed inside the organ 12'.

The shape of the organ 12' in the prototype image 10' now in a large extent conforms to the shape of the organ 22 in the target image 20. The labels of the labeled volume elements 16 in the prototype image 10 are now copied to corresponding volume elements 26 in the target image 20. Due to the deformation of the prototype image 10, the new labeled volume elements 26 in the target image 20 will be enclosed in the organ 22 in the target image 20.

To segment the organ 22 in the target image 20, the edge 24 of the organ 22 is detected and with a starting point in the labeled volume elements 26, an organ volume is defined and given the present label, according to a method of region-growing as presented above.

Figure 5:
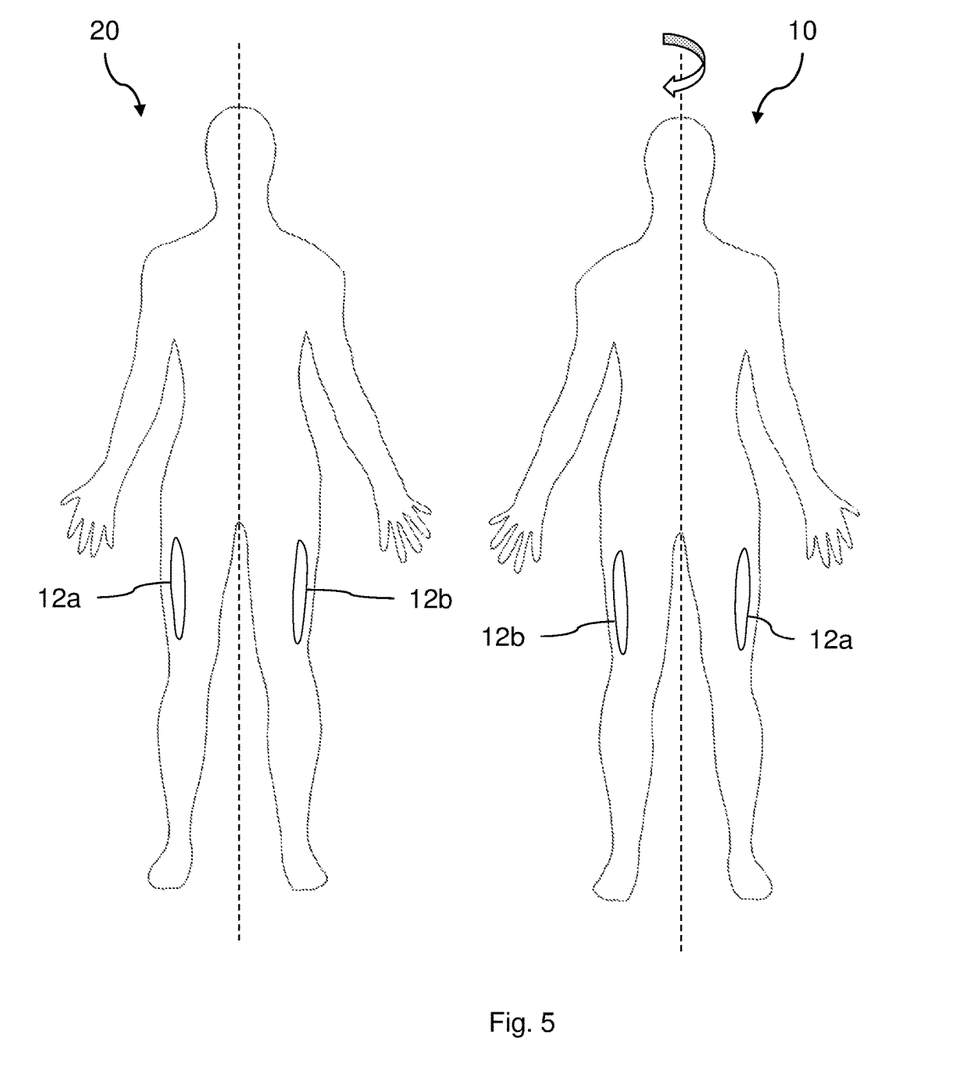
FIG. 5 shows a schematic view of a body image used in a method according to an embodiment of the invention.

FIG. 5 illustrates when the disclosed method is used performing asymmetry registration. Asymmetry registration may be used to identify differences between left and right body parts in a body. In that case, only one image is needed prior to the non-rigid co-registration. A mirrored copy of the target image 20 is used as prototype image 10. The prototype image 10, i.e. the mirrored copy, is deformed in order to fit the target image 20, i.e. the non-mirrored image. After that, the divergence of the resulting deformation field is determined. The divergence illustrates how each organ volume is expanded or compressed in order to fit the target image 20. An organ 12a in the left half of the target image 10 is used as basis for deformation of an organ 12b in the prototype image 20. The same organ 12b is used as a basis for deformation of the organ 12a in the prototype image 20. For instance, if the left organ 12a is larger than the right organ 12b, the right organ 12b in the prototype image 20 will be compressed, and the left organ 12a in the prototype image 20 will be expanded, when the prototype image 20 is deformed in order to fit the target image 10.

In the drawings and specification, there have been disclosed preferred embodiments and examples of the invention and, although specific terms are employed, they are used in a generic and descriptive sense only and not for the purpose of limitation, the scope of the invention being set forth in the following claims.

The invention claimed is:

1. A method for classification of organs in a tomographic image, the method comprising the steps of:
   receiving a 3-dimensional anatomical tomographic target image comprising a water image data set and a fat image data set, each of the water image data set and the fat image data set with a plurality of volume elements,
   providing a prototype image comprising a 3-dimensional image data set with a plurality of volume elements, wherein a sub-set of the volume elements of the prototype image are given an organ label,
   transforming the prototype image by applying a deformation field onto the volume elements of the prototype image such that each labeled volume element for a current organ is determined to be equivalent to a location for a volume element in a corresponding organ in the target image,
   transferring the labels of the labeled volume elements of the prototype image to corresponding volume elements of the target image, wherein similarly labeled volume elements in the target image define an organ volume representing a current organ,
   extending said organ volume to the entire organ based on properties in the target image,
   calibrating the target image based on labeled organs in the water image data set, wherein each labeled volume element in the target image is given a predetermined water value, and
   subtracting said predetermined water value with that labeled volume element's fat value in the fat image data set.

2. The method according to claim 1, wherein the step of extending the organ volume comprises detecting an edge of the organ in the target image.

3. The method according to claim 1, further comprising a step of manually entering a label to, or removing a label from, a volume element in the target image, wherein said manual step is followed by a redefinition of the organ volume referring to the present label.

4. The method according to claim 1, wherein the step of transforming the prototype image comprises applying a non-rigid co-registration of the prototype image onto the target image to increase the similarity between the prototype image and the target image, and wherein the non-rigid co-registration provides said deformation field representing a deformed prototype image.

5. The method according to claim 1, wherein said tomographic image is received from a magnetic resonance (MR) scanner or a computed tomography (CT) scanner.

6. The method according to claim 1, further comprising the step of removing the label of a first labeled volume element in the target image based on an analysis of said first labeled volume element compared to a similarly labeled second volume element in the target image.

7. The method according to claim 6, wherein said analysis comprises an analysis of said first labeled volume element in the water image data set and in the fat image data set compared to the similarly labeled second volume element in the water image data set and the fat image data set.

8. The method according to claim 6, wherein the step of removing the label of a first labeled volume element comprises determining a water-fat relationship for the first labeled volume element, comparing said water-fat relationship for the first labeled volume element with a corresponding water-fat relationship for the similarly labeled second volume element in the target image, and removing the first labeled volume element based on said comparison.

9. The method according to claim 6, wherein said analysis is based on the geometric location of the first labeled volume element and second labeled volume element in the target image.

10. The method according to claim 6, wherein the prototype image comprises an indicator on which said analysis is based.

11. The method according to claim 1, wherein the step of providing a prototype image comprises providing a plurality of prototype images, and
   wherein the step of transforming the prototype image comprises transforming the plurality of prototype images, which step is followed by a step of determining which of the transformed prototype images that best corresponds to the target image.

12. The method according to claim 1, wherein said prototype image is a mirrored copy of said target image.

13. The method according to claim 1, further comprising a step of interpolating the labeled volume elements into a homogeneous organ volume based on the predetermined water values in the labeled volume elements.

* * * * *